(12) United States Patent
Pressman et al.

(10) Patent No.: US 6,982,356 B2
(45) Date of Patent: *Jan. 3, 2006

(54) METHOD FOR PREPARATION OF PARA-BROMINATED HYDROXYAROMATIC COMPOUNDS

(75) Inventors: Eric James Pressman, East Greenbush, NY (US); Jonathan Lloyd Male, Schoharie, NY (US); Ryan Christopher Mills, Mechanicville, NY (US); John Yaw Ofori, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 99 days.

This patent is subject to a terminal disclaimer.

(21) Appl. No.: 10/664,093

(22) Filed: Sep. 17, 2003

(65) Prior Publication Data

US 2005/0059843 A1    Mar. 17, 2005

(51) Int. Cl.
*C07C 39/24* (2006.01)
(52) U.S. Cl. .................................................. 568/779
(58) Field of Classification Search .................. 568/779
See application file for complete search history.

(56) References Cited

U.S. PATENT DOCUMENTS

| | | | |
|---|---|---|---|
| 2,805,263 A | 9/1957 | Kaeding et al. | |
| 3,293,309 A | 12/1966 | Zemba | 260/623 |
| 3,987,068 A * | 10/1976 | Reilly | 552/296 |
| 6,410,774 B1 | 6/2002 | Grade et al. | |
| 6,815,565 B2 * | 11/2004 | Mills et al. | 568/779 |
| 2003/0032547 A1 | 2/2003 | Bonitatebus, Jr. et al. | |

FOREIGN PATENT DOCUMENTS

| | | |
|---|---|---|
| GB | 1269521 | 4/1972 |
| WO | WO 2004/064695 | 8/2004 |

OTHER PUBLICATIONS

K-J Lee et al., "Bromination of Activated Arenes by Oxone® and Sodium Bromide", *Bull. Korean Chem. Soc.* 23 (5), 773-74 (2002).
R. Neumann and I. Assael, "Oxybromination Catalysed by the Heteropolyanion Compound $H_sPMO_{10}V_2O_{40}$ in an Organic Medium: Selective para-Bromination of Phenol", *J. Chem. Soc., Chem. Commun.* 1285-87 (1988).
U. Bora et al., "Regioselective Bromination of Organic Substrates by Tetrabutylammonium Bromide Promoted by $V_2O_{5\text{-}}H_2O_2$: An Environmentally Favorable Synthetic Protocol", Org. Lett. 2 (3), 247-49 (2000).
K. Krohn et al., "Para-Selective Chlorination and Bromination of Phenols with tert-Butyl Hydroperoxide and TiX $(OiPR)_3$", *J. Prakt. Chem.* 341 (2), 59-61 (1999).
T. Oberhauser, "A New Bromination Method for Phenols and Anisoles: $NBS/HBF_4$ $ET_2O$ in $CH_3CN$", *J. Org. Chem.* 62, 4504-06 (1997).
N. Narender et al., "Liquid phase bromination of phenols using potassium bromide and hydrogen peroxide over zeolites", *J. Molec. Catalysis A: Chem.* 192, 73-77 (2003).
P.C. Th. M. Jonkheer et al., "Transsubstitution and equilibrium of phenols. Part III. Transbromination of phenols in the presence of aluminium phenoxide and other acidic catalysts", *Recl. Trav. Chim. Pays-Bas* 97, 223-6 (1978).
U.S. Appl. No. 10/341,475, filed Jan. 16, 2003, "Bromination of Hydroxyaromatic Compounds and Further Conversion to Dihydroxyaromatic Compounds".
U.S. Appl. No. 10/650,567, filed Aug. 28, 2003, "Selective Catalytic Oxybromination of Hydroxyaromatic Compounds".
U.S. Appl. No. 10/650,566, filed Aug. 28, 2003, "Bromination of Hydroxyaromatic Compounds".
PCT Search Report—Dec. 27, 2004.

* cited by examiner

*Primary Examiner*—Michael L. Shippen
(74) *Attorney, Agent, or Firm*—Andrew J. Caruso; William E. Powell, III

(57) ABSTRACT

A method for preparing hydroxyaromatic compounds brominated in the para-position, such as p-bromophenol, is disclosed. The method yields overall high process selectivity through isomeric equilibration and separation of the brominated products, thereby eliminating the need for high para selectivity in the products of catalytic oxybromination reactions of hydroxyaromatic compounds using oxygen, a bromine source, and an acidic medium in the presence of a metal catalyst. Furthermore, the invention provides an efficient method for recycling the metal catalyst, as well as reagents used in the bromination, to further reactions.

27 Claims, No Drawings

METHOD FOR PREPARATION OF PARA-BROMINATED HYDROXYAROMATIC COMPOUNDS

CROSS-REFERENCE TO RELATED APPLICATIONS

This Application is related to the following U.S. patent applications:

U.S. Ser. No. 10/342,475, filed Jan. 16, 2003 now abandoned, entitled "BROMINATION OF HYDROXYAROMATIC COMPOUNDS AND FURTHER CONVERSION TO DIHYDROXYAROMATIC COMPOUNDS";

U.S. Ser. No. 10/650,566, filed Aug. 28, 2003, entitled "BROMINATION OF HYDROXYAROMATIC COMPOUNDS"; and U.S. Ser. No. 10/650,567, filed Aug. 28, 2003, "SELECTIVE CATALYTIC OXYBROMINATION OF HYDROXYAROMATIC COMPOUNDS";

Each of these Applications is hereby incorporated by reference herein in its entirety.

BACKGROUND OF THE INVENTION

The present invention relates to the oxybromination of hydroxyaromatic compounds in the para position using a metal catalyst, and more particularly to increasing the yield of the desired brominated product and recycling the reagents.

Monocyclic dihydroxyaromatic compounds such as hydroquinone and dihydroxybiphenyls such as 4,4'-dihydroxybiphenyl ("biphenol") have numerous uses in the chemical industry. For example, both compounds can be used in polymer preparation, notably in the preparation of polycarbonates, polysulfones and polyimides, especially polyetherimides.

There are various methods for the preparation of hydroquinone and biphenol. As examples of such methods, each compound can be prepared from p-bromophenol, hydroquinone by hydrolysis and biphenol by reductive coupling in the presence of a noble metal catalyst, a base and a reducing agent.

Brominated hydroxyaromatic compounds, as exemplified by p-bromophenol, can be prepared by the method disclosed in the related co-pending commonly assigned U.S. patent application Ser. No. 10/342,475 filed Jan. 16, 2003. Briefly, the method comprises reacting the precursor hydroxyaromatic compound with a simple ionic bromide in an acidic medium, such as hydrobromic acid, and oxygen in the presence of a copper catalyst. Furthermore, as disclosed in the related co-pending commonly assigned U.S. patent application Ser. No. 10/650,566 filed Aug. 28, 2003, elemental bromine may be used as the bromine source in the bromination reaction. Also, related co-pending commonly assigned U.S. patent application Ser. No. 10/650,567 filed Aug. 28, 2003 discloses that a metal catalyst, such as one or more compounds or complexes of Group IV-VIII transition metals of the Periodic Table of Elements, may also be used to catalyze the bromination reaction.

While the above approach provides additional efficiencies, synthesis of p-bromophenol by reaction of brominating reagents with phenol is often complicated by the formation of undesired byproducts, most notably o-bromophenol. Thus, improved methods continue to be sought. Previous approaches have involved altering the conditions of the oxybromination reaction (e.g. process parameters, nature and concentration of catalyst), in order to reduce the level of the undesired o-bromophenol isomer. However, no set of reaction conditions to date has successfully yielded a 100% selective reaction to the desired p-bromophenol isomer. Another approach involves the separation (by distillation) of the o-bromophenol isomer followed by its palladium catalyzed reduction to bromide salt and phenol. While this is a high yield process, losses of organic substrate are observed, and use and losses of an expensive precious group metal catalyst are incurred.

Furthermore, in the catalytic preparation of brominated hydroxyaromatic compounds, it would be economical, and thus, highly desirable, if the reagents used in the process could be recycled to prepare additional products. In particular, it would reduce costs significantly in large-scale manufacturing operations if the metal catalyst used in the oxybromination reaction could be recovered and reused. The present invention meets these needs.

SUMMARY OF THE INVENTION

The present invention provides an efficient method for producing brominated hydroxyaromatic compounds, which virtually eliminates the need for high p-selectivity in the reaction products. The method yields overall high process selectivity through isomeric equilibration and separation. The method also provides a simple process for recycling of reagents used in the bromination reaction, and therefore reduces costs. Furthermore, the invention provides a simple method for recovering the metal catalyst for reuse, reducing costs even further.

Therefore, in one aspect, the invention relates to a method for recovering a metal catalyst for reuse, wherein the metal catalyst is selected from the group consisting of elemental copper, copper compounds, and one or more compounds or complexes of Group IV-VIII transition metals of the Periodic Table of Elements. The method comprises contacting a hydroxyaromatic compound with oxygen and a bromine compound selected from the group of hydrogen bromide, elemental bromine, ionic bromide salts, and mixtures thereof, in an acidic medium and in the presence of the metal catalyst to provide a reaction product mixture, followed by removing a portion of the reaction product mixture without removing the metal catalyst.

In another aspect, the present invention relates to a method of preparing a para-brominated hydroxyaromatic compound by an oxybromination reaction. The method comprises contacting in a reaction mixture a hydroxyaromatic compound with oxygen and a bromine compound selected from the group of hydrogen bromide, elemental bromine, ionic bromide salts, and mixtures thereof, in an acidic medium, in the presence of a metal catalyst selected from the group consisting of elemental copper, copper compounds, and one or more compounds or complexes of Group IV-VIII transition metals of the Periodic Table of Elements. A two-phase reaction product mixture comprising an organic phase and an aqueous phase is produced. The organic phase comprises the para-brominated hydroxyaromatic compound, a corresponding ortho-brominated hydroxyaromatic compound, and unreacted hydroxyaromatic compound. The aqueous phase comprises the metal catalyst, unreacted bromine compound, and the acidic medium. In the method, the organic phase of the product mixture is separated from the aqueous phase. At least a portion of water may optionally be removed from the aqueous phase. At least a portion of the metal catalyst in the aqueous phase, from which water has optionally been removed, is then recycled to a further oxybromination reaction of additional hydroxyaromatic compound employing oxygen and the bromine compound in the acidic medium.

In yet another aspect, a volatile organic solvent is also included in the aforementioned reaction mixture for the oxybromination reaction. The resulting reaction product mixture produced comprises the metal catalyst and a product-containing liquid comprising the para-brominated hydroxyaromatic compound, a corresponding ortho-brominated hydroxyaromatic compound, unreacted hydroxyaromatic compound, unreacted bromine compound, the acidic medium, and the volatile organic solvent. A major portion of the product-containing liquid is removed from the reaction product mixture. The removed major portion of the product-containing liquid comprises the corresponding ortho-brominated hydroxyaromatic compound, at least a portion of the para-brominated hydroxyaromatic compound, and a major portion of the unreacted hydroxyaromatic compound. The remaining reaction product mixture comprises the metal catalyst and the remaining product-containing liquid comprising any residual para-brominated hydroxyaromatic compound, and residual unreacted hydroxyaromatic compound. At least a portion of the metal catalyst from the remaining reaction product mixture is recycled to a further oxybromination reaction of additional hydroxyaromatic compound employing oxygen and the bromine compound in the acidic medium.

DETAILED DESCRIPTION OF THE PREFERRED EMBODIMENTS

The method of the present invention is particularly applicable to the oxybromination of hydroxyaromatic compounds using oxygen, a bromine compound in an acidic medium, and a metal catalyst, such as the method disclosed in co-pending, commonly assigned U.S. patent application Ser. No. 10/342,475, filed Jan. 16, 2003, co-pending commonly assigned U.S. patent application Ser. No. 10/650,566 filed Aug. 28, 2003, and co-pending commonly assigned U.S. patent application Ser. No. 10/650,567 filed Aug. 28, 2003.

The common initial reactant for all products obtained according to this invention is a hydroxyaromatic compound, such as a monocyclic monohydroxyaromatic compound. It may be an unsubstituted hydroxyaromatic compound such as phenol, or a substituted compound provided, however, that the 4-position is unsubstituted and thus available for bromination. As one of skill would know, the 2-, 3-, and 4-positions relative to the carbon attached to the hydroxy group are also known as and referred to herein as ortho-, meta-, and para-, respectively. Furthermore, o- refers to ortho-; m- refers to meta-; and p-refers to para-. Note that a substituent may be located at any position of the aryl ring other than the 1- or 4-carbons. Exemplary substituents (one or more) are alkyl groups, particularly $C_{1-4}$ alkyl. Illustrative compounds are those having the formula

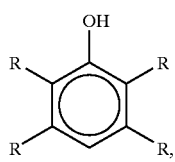

wherein each R is independently hydrogen or a substituent, preferably $C_{1-4}$ alkyl.

Examples of hydroxyaromatic compounds include phenol, o-cresol, m-cresol; 2,6-xylenol; 2,5-xylenol; 2,3,5-xylenol; 2,3,6-xylenol; 2-ethylphenol, 2-propylphenol, 2-tert-butylphenol, 2-phenylphenol, and the like. Typically, phenol, m-cresol, and o-cresol are preferred. Specific reference will be frequently made to phenol hereinafter.

In the oxybromination reaction, the hydroxyaromatic compound is contacted with oxygen and a bromine compound in the presence of a metal catalyst. The oxygen is employed in stoichiometric excess and may be pure oxygen or may be employed in the form of air or oxygen-enriched air. Contact may be with flowing oxygen or air or under pressure, typically up to about 100 atm.

Suitable bromine compounds include hydrogen bromide, elemental bromine ($Br_2$), and bromide salts. Mixtures may also be used in the bromination reaction. Hydrogen bromide may be employed in any form; examples are gaseous HBr, aqueous HBr (hydrobromic acid) and HBr in solution in a polar organic solvent, typically one of the solvents described hereinafter. Bromide salts include alkali metal bromides such as sodium bromide and potassium bromide and alkaline earth metal bromides such as calcium bromide and magnesium bromide. Hydrobromic acid is generally the preferred bromine compound. It may be employed at any concentration, including the commercially available 48% by weight aqueous solution.

The contact is in an acidic medium. Aqueous acidic media including Brønsted acids generally, and particularly including sulfuric acid, phosphoric acid and nitric acid, may be employed; or, if hydrobromic acid is the bromine compound employed, it may serve as the acidic medium. Volatile organic solvents may also be present. These include, but are not limited to, acetonitrile (bp 81–82° C.), chloroform (bp 61° C.), ethyl acetate (bp 76.5–77.5° C.), o-dichlorobenzene (bp 180° C.), acetic acid (bp 117–118° C.), and propionic acid (bp 141° C.). As used herein, the term "volatile organic solvent" means a polar organic solvent having a lower boiling point than any of the brominated products, such as 2-bromophenol having a boiling point of 195° C., but preferably, lower than that of the hydroxyaromatic compound. For example, phenol has a boiling point of 182° C. Acetic acid and acetonitrile having boiling points of 117–118° C. and 81° C., respectively, are frequently preferred. In addition, water and excess hydroxyaromatic compound may also be present. Mixtures of the foregoing solvents may also be employed. Often the reaction medium will be anhydrous.

The oxybromination reaction occurs in the presence of a metal catalyst, such as elemental copper, a copper compound, or one or more compounds or complexes of Group IV-VIII transition metals of the Periodic Table of Elements, as described in U.S. patent application Ser. No. 10/650,567 filed Aug. 28, 2003.

When copper is used to catalyze the reaction, copper compounds are generally used. Examples are cupric sulfate, cupric chloride, cupric bromide, cuprous chloride and cuprous bromide. Of these, cupric bromide ($CuBr_2$) is often employed by reason of its relatively low cost and particular suitability, as contact with hydrobromic acid will usually convert other cupric salts to the bromide. A molar ratio of hydroxyaromatic compound to the copper catalyst ranging from about 10:1 to about 200:1 is sufficient to catalyze the reaction. A ratio of 30:1 is typical.

When a compound/complex of a transition metal from Group IV-VIII of the Periodic Table of Elements is employed as the catalyst, suitable transition metals include vanadium, titanium, molybdenum, tungsten, and iron, for example. Vanadate salts, such as sodium metavanadate having the chemical formula $NaVO_3$, are often used. Other suitable transition metal catalysts include, for example, bis(acetylacetonate)oxovanadium ($VO(acac)_2$), bis(acetylacetonate)oxotitanium ($TiO(acac)_2$), sodium molybdenum oxide dihydrate ($NaMoO_4\ 2H_2O$), iron bromide ($FeBr_2$), and tungstic acid ($H_2WO_4\ xH_2O$). Bis(acetylacetonate)oxovanadium has the chemical formula $VO(CH_3COCHCOCH_3)_2$, and bis(acetylacetonate)oxotitanium has formula $TiO(CH_3COCHCOCH_3)_2$. In addition, the Group IV-VIII transition metal catalyst compounds may be used alone or in combination, such as in a mixture. However, the invention is not limited to use of these transition metal catalysts, and other metals, ligands, and salts will be obvious to those of skill.

A molar ratio of hydroxyaromatic compound to the transition metal catalyst(s) ranging from about 1:1 to about 500:1 minimizes conversion of the products to dibromo and more highly brominated compounds. Typically, a molar ratio of 200:1 is employed.

The bromination reaction may be conducted at a temperature in the range of about 20–150° C., but generally about 60–100° C. Proportions of copper source are most often in the range of about 0.1–30 mole percent of copper based on hydroxyaromatic compound. The molar ratio of ionic bromide to hydroxyaromatic compound is preferably less than 1:1, to minimize conversion to dibromo and more highly brominated compounds; ratios in the range of about 0.2–0.9:1 are typical. When elemental bromine is the bromine source, the molar ratio of $Br_2$ to hydroxyaromatic compound is preferably less than 1:2, typically in the range of about 0.2–0.9:2, again to minimize the formation of by-products.

The product of the oxybromination reaction is usually predominantly the p-bromo compound, with minor amounts of o-bromo compound and dibromo and higher compounds also being present. Conversion of phenol to bromophenols is usually at least 40%, "conversion" being defined as total phenol in weight units or moles consumed as a percentage of phenol originally present. Selectivity to 4-bromophenol is usually at least 80% and often greater than 90%, "selectivity" meaning moles of the specific product formed as a percentage of moles of hydroxyaromatic compound consumed. Furthermore, "monobromoselectivity" is defined herein as moles of para-brominated and ortho-brominated product formed as a percentage of moles of para-brominated products, ortho-brominated products, dibrominated products, and more highly brominated products formed.

Depending on the reagents used, the reaction product mixture is either one phase or two-phases. For example, when excess hydroxyaromatic compound is the only solvent in a reaction using hydrobromic acid as the brominating agent as well as the acidic medium, the product reaction mixture will be split into an organic phase and an aqueous phase. However, if a volatile organic solvent is included with the reactants, the reaction product mixture may be in only one phase.

As previously mentioned, it is advantageous to recover the metal catalyst from the bromination reaction for reuse. In the case where a two-phase reaction product mixture is provided, the majority of the metal catalyst is found in the aqueous phase. To recover the catalyst, the two phases are separated using conventional techniques, such as by decantation, or by using a separatory funnel, a separation tank, or a continuous separation column, for example, and the organic phase is removed. The recovered catalyst in the aqueous phase can then be recycled in a further bromination reaction if desired. However, prior to recycling the catalyst, it is often desirable to remove some of the water from the aqueous phase. This can be done by commonly known techniques, such as by vacuum distillation. In some instances, it may be desirable to remove all the water. This can be done by concentrating the aqueous phase into a solid, which comprises the catalyst, using ordinary techniques such as distillation followed by drying. In either case, the recovered metal catalyst is ready for reuse and can then be recycled into another oxybromination reaction.

When a volatile organic solvent, such as one previously listed, is included in the aforementioned oxybromination reaction mixture, a one phase reaction product mixture may be produced. In this case, the metal catalyst may be recovered by removing a portion of the product mixture, typically by distillation. The metal catalyst in the remaining product mixture is ready for reuse, such as being recycled into another oxybromination process. If desired, the remaining product mixture may be concentrated into a solid, which contains the metal catalyst, prior to reuse.

As previously mentioned, the bromination reaction described herein produces mainly the desired p-bromo hydroxyaromatic compound. However, undesirable by-products, such as minor amounts of o-bromo compound are also produced. Minor amounts of dibromo-products may also be present. Advantageously, the present method increases the yield of the useful p-bromo product by isomerization of the corresponding o-bromo compound. Furthermore, any dibrominated products can be converted to the monobrominated compound by isomerization, as described herein, provided there is enough hydroxyaromatic compound present to accommodate the extra bromine equivalent.

According to the present method, when a two-phase reaction product is obtained from the previously described oxybromination reaction, the organic phase includes the para-brominated hydroxyaromatic compound, the corresponding ortho-brominated hydroxyaromatic compound, and a major portion of the unreacted hydroxyaromatic compound. Typically, traces of unreacted bromine compound, traces of the metal catalyst, as well as other by-products, will be present in the organic phase. The aqueous phase contains the majority of the metal catalyst, most of the unreacted bromine compound, the acidic medium, and any residual unreacted hydroxyaromatic compound not present in the organic phase.

The organic phase is then separated from the aqueous phase using conventional techniques, such as those mentioned above. The metal catalyst, which is included in the aqueous phase, may then be recycled for use in another oxybromination reaction, as previously described. In general, the unreacted bromine compound, the acidic medium, and any residual hydroxyaromatic compound in the aqueous phase are also recycled to another oxybromination reaction. Usually, a portion of the water is removed prior to recycling.

After separating the organic and aqueous phases, it is preferable to wash the organic phase with water at least one time, but preferably up to three times, to remove any traces of the bromine compound, as well as any traces of the metal catalyst. The wash water is then removed and may be combined with the aqueous phase for recycling to another bromination reaction. Again, much of the water is typically removed prior to recycling.

After separating the organic phase and optionally washing it with water, the organic phase is typically separated into four fractions: a first fraction containing unreacted hydroxyaromatic and any water present, a second fraction containing the o-brominated hydroxyaromatic, a third fraction containing the p-brominated hydroxyaromatic, and a fourth fraction containing any dibrominated species, which have higher boiling points than the preceding fractions. Separation of these compounds may be effected by art-recognized methods, such as fractionation by vacuum distillation, steam distillation, reactive distillation, sublimation, crystallization, zone refining and like techniques, or a combination of one or more of such techniques. Typically, fractional distillation is preferred, because, for example, there is a difference of more than 40° C. between the boiling points of 2-bromophenol (194.5° C.) and 4-bromophenol (238° C.). One to three distillations are generally sufficient. Distillation may be conducted under reduced pressure to minimize thermal decomposition.

While isolating the para-brominated hydroxyaromatic compound from the organic phase in the third fraction, typically by distillation, a stream (i.e., second fraction) is also produced, which comprises the corresponding ortho-brominated hydroxyaromatic compound. However, para-brominated hydroxyaromatic compound, as well as dibrominated product may also be included in the stream. The ortho-brominated product stream may also comprise unreacted hydroxyaromatic compound.

In one embodiment the para-brominated hydroxyaromatic compound is not removed as a separate fraction from the organic phase, and a stream comprising both the para-brominated product and the ortho-brominated product may be collected as the distillate.

In order to increase the yield of the para-brominated product, the undesired ortho-bromo compound in the distillate stream may then be subjected to an isomerization reaction to convert the ortho to the desired para-brominated product, as described in U.S. Pat. No. 3,293,309 to Zemba. Briefly, the stream, which contains the ortho-bromo product, and optionally the para-bromo product, is contacted with additional hydroxyaromatic compound and aqueous hydrogen bromide to form a pre-equilibration mixture, which is then heated to a temperature ranging from about 25° C. to about 200° C. The ortho-brominated compound, and optionally the para-compound, is equilibrated to a mixture of p-bromo-compound:o-bromo-compound having an equilibrium constant typically about 0.8 (at 150° C.). Aqueous hydrogen bromide acts as the acidic catalyst for the isomerization reaction. The amount of aqueous hydrogen bromide is not critical, so long as it is sufficient to be catalytically effective. As little as 0.01% or as much as 10% by weight of the reaction mixture may be employed. Usually, from 0.1% to 2% by weight is suitable.

The isomerization process is conducted at a temperature ranging from about 25° C. to about 200° C. However, a temperature of about 150° C. is often employed. After heating the pre-equilibration mixture for a sufficient time to equilibrate the isomers, generally ranging from about 15 minutes to about 24 hours, a post equilibration solution is formed. The post equilibration solution comprises the otho-brominated hydroxyaromatic compound and the para-brominated hydroxyaromatic compound in equilibrium, as well as any unused hydroxyaromatic compound, and aqueous hydrogen bromide.

After the equilibration is complete, the post equilibration solution may be recycled to a further oxybromination reaction of the unused hydroxyaromatic compound and additional hydroxyaromatic compound employing the metal catalyst, oxygen, and aqueous hydrogen bromide. However, it may often be desirable to isolate the para-brominated product from the post equilibration solution prior to its being recycled in a further bromination reaction. As previously mentioned, the para-brominated and ortho-brominated compounds may be separated by vacuum distillation, for example, and the ortho-brominated compound can then be returned to the remaining post equilibration solution for recycling.

In one embodiment, when aqueous hydrogen bromide is employed in the initial oxybromination reaction as the bromine compound, as well as the acidic medium, unreacted aqueous hydrogen bromide residing in the aqueous phase from the oxybromination reaction may then be removed from the aqueous phase, typically by distillation, and recycled for use in the above-described isomerization reaction.

When a volatile organic solvent is included in the oxybromination reaction of the hydroxyaromatic compound described, a one-phase product mixture may be produced. This single phase mixture comprises the metal catalyst, as well as a product-containing liquid. The para-brominated hydroxyaromatic compound, as well as the corresponding ortho-brominated hydroxyaromatic compound, unreacted hydroxyaromatic compound, any unreacted bromine compound, the acidic medium and the volatile organic solvent are included in the product-containing liquid. After the bromination step, the majority of the product-containing liquid is removed from the reaction product mixture, typically by distillation, to remove the ortho-brominated hydroxyaromatic compound and at least a portion of the para-brominated hydroxyaromatic compound. Generally, when aqueous hydrogen bromide is employed, the volatile organic compound, most of the unreacted aqueous hydrogen bromide and a major portion of the unreacted hydroxyaromatic compound, such as phenol having a boiling point of 182° C., will also be removed during the distillation. However, if desired, the unused aqueous hydrogen bromide having a boiling point of approximately 126° C. (47 wt. %) may be removed, typically by distillation, prior to removing the majority of the product-containing liquid, and recycled to a further oxybromination reaction.

However, it is often beneficial to remove the volatile organic solvent from the product-containing liquid, typically by distillation, prior to removing the portion containing the brominated products. The volatile organic solvent can then be recycled to another oxybromination reaction. When aqueous hydrogen bromide is employed as the bromine source in the acidic medium, unused aqueous hydrogen bromide will often also be removed and recycled with the volatile organic solvent.

The metal catalyst, as well as any residual amounts of para-brominated hydroxyaromatic compound and residual unreacted hydroxyaromatic compound reside in the remaining reaction product mixture. Residual unreacted bromine compound and residual acidic medium are typically included in the remaining reaction product liquid also. The metal catalyst is then recycled to a further bromination reaction, as well as the remaining product mixture, if desired.

In one embodiment, the removed portion of the product-containing liquid may be washed with water, one to three times, to remove any bromine compound, any acidic medium, and any traces of the metal catalyst. The wash water may then be removed and recycled with the recovered metal catalyst to another oxybromination reaction. Optionally, a portion of the water from the wash water is removed prior to recycling.

Furthermore, the desired para-brominated product may be isolated from the removed major portion of the product liquid, typically by distillation followed by crystallization. The stream containing the ortho-brominated product and any residual para-bromo compound is then subjected to an isomerization reaction to increase the yield of the para-brominated product, followed by recycling the post equilibration solution to a further oxybromination reaction, as previously described. However, the majority of para-brominated product may instead undergo the isomerization, if desired. Unreacted hydroxyaromatic compound from the oxybromination reaction is often also included in the stream prior to isomerization. When aqueous hydrogen bromide is employed in the initial bromination reaction, unused aqueous hydrogen bromide may also be included in the stream undergoing the isomerization reaction.

Furthermore, after the isomerization, the para-brominated product may be isolated from the post equilibration solution prior to recycling.

The following examples are given by way of illustration and are not intended to be limitative of the present invention. The reagents, reactants, and catalysts used in the oxybromination reaction described herein are readily available materials. Such materials can be conveniently prepared in accordance with conventional preparatory procedures or obtained from commercial sources.

In the following examples, phenol is the hydroxyaromatic compound, 48 wt. % aqueous HBr is the bromine compound and acidic medium, and the metal catalyst is cupric bromide. However, the invention is not limited to the bromination of phenol, and other hydroxyaromatic compounds, such as o-cresol, m-cresol, or any of the other previously mentioned compounds, may be substituted for phenol. In addition, other brominating compounds, acidic mediums, and metal catalysts, such as those previously mentioned may be used instead. As used herein, the terms "eq." and "equivalent" mean molar equivalent.

EXAMPLE 1

Bromination of Phenol-Two Phase

To a Parr autoclave reactor fitted with a glass liner was charged phenol (61.07 g, 650 mmol, 1 eq.), 48% HBr (81.08 g, 480 mmol, 0.74 eq.) and $CuBr_2$ (3.6 g, 1.6 mmol, 0.0025 eq.). The mixture was heated at 65° C. under 34 atm of air for 30 minutes. The resulting two-phase mixture was separated using a separatory funnel, and each phase was analyzed using standard GC techniques. The total mixture was found to contain the following: phenol (41.1 g, 437.10 mmol, 49.91 wt. %); 4-bromophenol (29.8 g, 172.00 mmol, 35.73 wt. %) and 2-bromophenol (5.1 g, 29.67 mmol, 6.17 wt. %), corresponding to 32.6% conversion of phenol with 81.2% selectivity for 4-bromophenol, a total monobromophenol selectivity of 95.2%, and a total phenolic mass balance of 98.4%. No analysis was done for copper, but see Example 5. The HBr conversion to bromophenols was 42%. After separating the organic phase from the aqueous phase, the organic phase was found to contain ~97% of the organics, with only trace amounts present in the aqueous phase (containing most of the catalyst) of which the major component was phenol. In particular, the organic phase contained phenol (39.40 g, 418.71 mmol, 47.15 wt. %); 4-bromophenol (29.45 g, 170.20 mmol, 35.23 wt. %); and 2-bromophenol (5.08 g, 29.33 mmol, 6.07 wt. %). The aqueous phase contained phenol (1.73 g, 18.39 mmol, 2.76 wt%); 4-bromophenol (0.31 g, 1.80 mmol, 0.50 wt. %); 2-bromophenol (0.06 g, 0.34 mmol, 0.09 wt. %), copper (not analyzed), and unreacted aqueous HBr (not analyzed).

EXAMPLE 2

The organic phase (83.56 g) from Example 1 is washed with water (10 g) to remove traces of Cu and HBr, and the wash aqueous phase (about 10 g) is separated from the washed organic phase (about 83 g). The aqueous wash phase (about 10 g) is combined with aqueous phase from Example 1 containing the bulk of the catalyst (about 62.68 g).

EXAMPLE 3

Separation of Brominated Products and Isomerization

The organic phase from Example 2 is distilled into a low-boiling fraction (about 49 g), containing the majority (>98%) of the water and phenol present, and also containing traces of brominated compounds, a medium-boiling fraction (about 8 g) containing >98% of the 2-bromophenol and <10% of the 4-bromophenol, and a high-boiling fraction (about 26 g), containing primarily 4-bromophenol, which exits the process. The medium-boiling fraction is isomerized by adding aqueous HBr (about 2 g of aqueous HBr, 48%) and phenol (about 15 g), and heating the resulting pre-equilibrium mixture to 150° C. for 20 minutes. The isomerization results in a post equilibration mixture where the ratio of 2-bromophenol to 4-bromophenol is about 1:1.

EXAMPLE 4

Catalyst Recycle, Bromination of Additional Phenol

The procedure of Example 1 is followed except that the Parr autoclave reactor is charged with the post equilibration mixture from Example 3, additional phenol, HBr (as 48% aqueous solution), and the copper catalyst (about 62.68 g) from Example 2, which is obtained by combining the aqueous phase from the initial bromination reaction of Example 1 and the wash water of Example 2, followed by evaporating about 8.63 g of the water. The water is removed to prevent water from accumulating in the process: about 3.63 g of water is produced during bromination of phenol, and 5 g of water is added from the wash water of Example 2.

EXAMPLE 5

Seventeen (17) glass vials, each containing a magnetic stir bar, were each charged with 3.6 grams (38.25 mmol, 1 equivalent) phenol, 5.1 grams 48% aq HBr (30.25 mmol, 0.79 eq.), and 0.34 grams (1.5 mmol, 0.040 eq.) $CuBr_2$. Each vial was fitted with a screw cap containing a hole to allow for pressure equilibration, and placed in a separate fitted cavity in an aluminum block which was inserted into an autoclave adapted for magnetic stirring of multiple samples. The total amount charged to the reaction was 61.2 grams phenol (650 mmol, 1 eq.), 86.7 grams (514 mmol, 0.79 eq.) 48% aq HBr, and 5.78 grams (25.9 mmol, 0.040 eq.) $CuBr_2$, of which 1.6341 grams (25.71 mmol, 0.039 eq.) were copper. The mixtures were pressurized with 34 atm air and heated to 65° C. for 2 hrs. Upon cooling, the mixtures were combined in a separatory funnel, and the resultant two phases were separated. The compositions of each phase were analyzed by HPLC (high performance liquid chromatography) and ICP (inductively coupled plasma spectroscopy). The organic phase was found to contain 54.02 grams of phenol, 1.45 grams of 2-bromophenol, 8.60 grams of 4-bromophenol, and 0.0258 grams of copper (by ICP). The aqueous phase, having a total weight of 74.32 grams, was found to contain 2.76 grams phenol and 1.5384 grams of copper (by ICP). The bromophenol/2-bromophenol selectivity was 6/1, and mass, phenol, and copper balances were all high (at least 96%), corresponding to 9% phenol conversion and 11% HBr conversion. The low conversions were due to limited oxygen supply. Typically, conversion of $O_2$ based on an estimation of the head space volume and comparing the moles of $O_2$ in that volume at the starting pressure to the moles of brominated products is about 100%. The reactor used in this example had a limited headspace volume, which became depleted in $O_2$ very rapidly.

EXAMPLE 6

The organic phase from Example 5 is washed with water to remove aqueous hydrogen bromide and catalyst traces. The wash water is then combined with the aqueous phase from Example 5, and a portion of the total amount of water is removed. The resulting aqueous mixture is recycled to a subsequent reaction.

EXAMPLE 7

Separation of Brominated Products

Forty (40) grams of the organic phase from Example 5 containing 27.02 grams (287 mmol, 1 eq.) phenol, 0.72 grams (4.16 mmol, 0.014 eq.) 2-bromophenol, and 4.02 grams (23.24 mmol, 0.081 eq.) 4-bromophenol, and 0.013 grams (0.21 mmol, 0.0007 eq.) of copper were vacuum distilled at 0.1 mm Hg to ultimate pot and head temperatures of 65° C. and 53° C., respectively, to separate the brominated products. The distillate was collected in two receivers connected in series, the second of which was cooled in liquid nitrogen. As indicated by HPLC analysis, the first receiver was found to contain 12.66 grams phenol, 0.23 grams of 2-bromophenol, and 1.07 grams of 4-bromophenol. The material collected in the second receiver separated into two phases. The aqueous phase, which had a total weight of 2.92 grams, was found to contain 0.27 grams phenol and 0.01 grams 2-bromophenol, the remainder being unreacted HBr. This phase is subsequently recycled to another reaction. The organic phase in the second receiver was found to contain 10.93 grams phenol, and 0.09 grams of 4-bromophenol. Remaining in the pot were 0.80 grams phenol and 3.11 grams 4-bromophenol. No analysis was done for copper in the receivers or pot; it was assumed that all the copper was in the pot. Both of the isomeric bromophenol balances (i.e., 4-bromophenol and 2-bromophenol) were close to theory (99–102%) indicating no loss or equilibration during the distillation. Additional distillations are performed to isolate a pure fraction of 4-bromophenol, which exits the process.

EXAMPLE 8

Isomerization

The contents of the first receiver from Example 7 containing 12.66 grams (135 mmol) of phenol, 0.23 grams (1.33 mmol) of 2-bromophenol, and 1.07 grams (6.19 mmol) of 4-bromophenol are combined with the contents remaining in the pot after the distillations of Example 6, i.e., 0.80 grams (8.50 mmol) phenol and 3.11 grams (17.98 mmol) 4-bromophenol, and 0.013 grams (0.21 mmol) of copper. To this mixture is added 7.5 mmol of unreacted aq HBr from the aqueous phase in the second receiver of Example 7. The resulting pre-equilibration mixture is heated at 150° C. for ~20 minutes to enrich the level of 4-bromophenol (by bromophenol equilibration), and the entire post equilibration mixture is recycled to a subsequent bromination reaction.

EXAMPLE 9

Separation of Brominated Products

A mixture of the organic and aqueous phases (40.44 grams) in the same proportion as that obtained in Example 5 was vacuum distilled at 0.04 mm Hg to ultimate pot and head temperatures of 67° C. and 50° C. respectively. Prior to distillation, the mixture contained 13.92 grams (148 mmol) of phenol, 0.35 grams (2.02 mmol) of 2-bromophenol, 2.09 grams (12.08 mmol) of 4-bromophenol, and 0.44 grams (6.92 mmol) of copper. The distillate was collected in two receivers connected in series, the second of which was cooled in liquid nitrogen. As indicated by HPLC analysis, the first receiver was found to contain 3.14 grams phenol, 0.03 grams of 2-bromophenol, and 0.47 grams of 4-bromophenol. The material collected in the second receiver separated into two phases. The aqueous phase had a total weight of 21.55 grams, of which 1.03 grams was phenol. The remainder was mostly unreacted aqueous HBr. The organic phase in the second received was found to contain 6.68 grams phenol, 0.30 grams 2-bromophenol, and 0.05 grams of 4-bromophenol. Remaining in the pot were 0.74 grams phenol and 1.51 grams 4-bromophenol. No analysis was done for copper in the receivers or pot; it was assumed that all the copper (0.44 grams) was in the pot. Both of the isomeric bromophenol balances are close to theory (96–97%), indicating no loss or equilibration during the distillation, even in the presence of all the Cu normally associated with the bromination reaction. The slightly lower total and phenol balances were attributed to loss of some water and PhOH through the single liquid $N_2$ cooled vessel at high vacuum. The aqueous phase in the second receiver, containing primarily unreacted aqueous HBr and ~5 wt % PhOH, is recycled to another reaction.

EXAMPLE 10

Isomerization

To the remaining contents of the pot of Example 9, which contained 0.74 grams (7.86 mmol) of phenol, 1.51 grams (8.73 mmol) of 4-bromophenol, and 0.44 grams (6.92 mmol) of copper, was added the organic phase of the second receiver of Example 9, which contained 6.68 grams (70.98 mmol) of phenol, 0.30 grams (1.73 mmol) of 2-bromophenol, and 0.05 grams (0.29 mmol) of 4-bromophenol. To the resulting mixture was added 1.03 grams (10.95 mmol) of phenol and 5.34 grams (31.68 mmol) of unreacted aq HBr from the aqueous phase in the second receiver of Example 9, as well as 10.32 additional grams (110 mmol) of phenol. The resulting pre-equilibration mixture was heated at 150° C. for 20 minutes, and the resulting post-equilibration mixture was found by HPLC analysis to contain 18.64 grams phenol, 1.01 grams 2-bromophenol, and 0.82 grams of 4-bromophenol. No analysis was done for Cu; but it is assumed that the 0.44 grams of copper was in the post-equilibration mixture, and that the Cu balance is 100%. The ratio of 4-bromophenol/2-bromophenol of 0.81/1 is comparable to that obtained under similar conditions following equilibration of synthetic solutions that do not contain any Cu compounds. Thus, the copper catalyst present that derive from the Examples 5 and 9 did not impede the isomerization.

EXAMPLE 11

Catalyst Recycle

A Parr autoclave reactor fitted with a glass liner was charged with a portion of the post-equilibration mixture (19.28 grams) from Example 10 containing 1.77 grams (7.93 mmol) $CuBr_2$ (containing 0.2 grams (3.14 mmol) of Cu), 12.57 grams (134 mmol) of phenol, 0.68 grams (3.93 mmol) of 2-bromophenol, 0.55 grams (3.18 mmol) of 4-bromophenol, and 3.79 grams (22.48 mmol) of 48% aqueous HBr. To this mixture was added 63.33 grams (673 mmol) of phenol, and 81.95 grams (486 mmol) of 48% aqueous HBr. The resulting mixture was pressurized with 38 atm air and heated to 70° C. for 2 hrs, while stirring at 1400 rpm. The approximate headspace volume was 500 mL. Upon cooling, the organic and aqueous phases were separated using a separatory funnel. The compositions of each phase were analyzed by HPLC. The organic phase was found to contain 56.07 grams of phenol, 4.17 grams of 2-bromophenol and 21.35 grams of 4-bromophenol. The aqueous phase was found to contain 1.98 grams of phenol, 0.04 grams of 2-bromophenol, and 0.12 grams of 4-bromophenol. The mass balance was 95.6%; the phenol conversion was 22.5%; the yield of bromophenols based on HBr charged was 20.0%, and the phenol mass balance was 96.1%. The performance of the recycled catalyst from Example 10 corresponded well with a reaction run under comparable conditions using virgin cupric bromide as the catalyst.

EXAMPLE 12

Catalyst Recovery 48.24 Grams of the aqueous phase from Example 5 (containing 1.0 grams Cu) were concentrated by vacuum distillation at 2.3 mm Hg to ultimate pot and head temperatures of 35° C. and 30° C., respectively. The distillate was collected in two receivers connected in series, the second of which was cooled in liquid nitrogen. 43.8 Grams of white distillate were collected and shown by HPLC to contain 0.8 grams (8.5 mmol) of phenol, and the balance was aq HBr (255 mmol). This distillate is recycled in its entirety to another bromination reaction, as described in Example 5. The pot contained of 3.57 grams of a dark solid, of which 1.0 grams is assumed to be copper, and the balance was ~40:60 phenol:aq HBr mixture (via phenol mass balance vs. pot and distillates). This copper rich sample was ready for recycling.

EXAMPLE 13

Catalyst Recycle

A Parr autoclave reactor fitted with a glass liner was charged with 62.33 grams (0.66 mol) phenol, 83.3 grams (494 mmol) of 48% aq HBr (0.49 mol), and the 3.57 gram solid (containing used cupric bromide) from Example 12. The mixture was pressurized with 38 atm air and heated to 70° C. for 2 hrs, while stirring at 1400 rpm. The approximate headspace volume was 500 mL. Upon cooling, the organic and aqueous phases were separated using a separatory funnel. The compositions of each phase were analyzed by HPLC. The organic phase was found to contain 33.6 grams of phenol, 5.78 grams of 2-bromophenol and 31.31 grams of 4-bromophenol. The aqueous phase, having a total weight of 57.80 grams, was found to contain 1.27 grams of phenol, 0.05 grams of 2-bromophenol, and 0.22 grams of 4-bromophenol. The mass balance was 92.1%; the phenol conversion was 44.0%; the yield of bromophenols based on aq. HBr charged was 44.1%, and the phenol mass balance was 88.6%. The performance of the recycled catalyst from Example 12 corresponded well with a reaction run under comparable conditions using virgin cupric bromide as the catalyst.

EXAMPLE 14

Bromination of Phenol-One Phase

A Parr autoclave reactor fitted with a glass liner was charged with phenol (23.7 g, 225 mmol), 48% aqueous HBr (40.2 g, 238 mmol), $CuBr_2$ (1.79 g, 8.01 mmol) and acetonitrile (30.5 mL). The mixture was heated at 65° C. under 34 atm of air for 1 hour. The resulting single phase mixture was analyzed using standard GC techniques. The mixture was found to contain 5.44 g of phenol, 26.13 g of 4-bromophenol, and 5.00 g of 2-bromophenol, corresponding to 76.5% conversion of phenol with 80% selectivity for 4-bromophenol, a total monobromophenol selectivity of 95%, and a total phenolic mass balance of 98%. The HBr conversion to bromophenols was 79%, leaving 4.04 grams HBr in the mixture. In addition to the water added with the HBr (aq) (20.9 g), 3.4 g of water was produced during the reaction (based on bromophenol formed). The copper catalyst was also included in the product mixture, but no analysis was conducted for it.

EXAMPLE 15

Recovery of Reagents

The single phase mixture from Example 14 is distilled to remove unreacted aqueous HBr, acetonitrile, a minor portion of water, and trace phenol as one fraction, which is then recycled to a subsequent oxybromination reaction.

EXAMPLE 16

Separation of Brominated Products

The mixture remaining after the distillation of Example 15 contains phenol, 2-bromophenol, 4-bromophenol, the copper catalyst, and water. This mixture is distilled at reduced pressure to provide a phenol-water fraction, a second fraction containing 2-bromophenol and a major portion of 4-bromophenol, and a pure fraction of 4-bromophenol, which exits the process. The phenol-water fraction is sufficiently dried to prevent water build-up, and is ready for recycling. After the distillations, a mixture containing a minor portion of 4-bromophenol, trace amounts of 2,4-dibromophenol, and the copper catalyst remains in the vessel.

EXAMPLE 17

Isomerization

To the mixture of 4-bromophenol, 2,4-dibromophenol, and copper catalyst remaining in the vessel after the distillations of Example 16 is added aqueous HBr. The dried phenol-water fraction from Example 16 is also added, as well as additional phenol. The resulting mixture is combined with the second fraction from Example 16 containing 2-bromophenol and a major portion of 4-bromophenol, and the combination mixture is heated at 150° C. for ~20 minutes to enrich the level of 4-bromophenol (by bromophenol equilibration). The amount of aq HBr needed for the equilibration may be as little as 0.01% or as much as 10% by weight of the reaction mixture. In practice, aq HBr is often added to the reaction mixture until no additional improvement in the equilibration rate is observed. Usually, from 0.1% to 2% by weight is suitable. However, in some cases it may be desirable to add enough aq HBr to the equilibration reaction as is needed in the subsequent bromination. After the equilibration, the entire mixture is recycled (with additional aq HBr if necessary) to a subsequent bromination reaction, with equivalent activity and performance of the recycled copper catalyst to that described in Example 11.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for recovering a metal catalyst for reuse, wherein said metal catalyst is selected from the group consisting of elemental copper, copper compounds, and one or more compounds or complexes of Group IV-VIII transition metals of the Periodic Table of Elements, wherein said method comprises:
    (a) providing a reaction product mixture by contacting a hydroxyaromatic compound with oxygen and a bromine compound selected from the group of hydrogen bromide, elemental bromine, ionic bromide salts, and mixtures thereof, in an acidic medium and in the presence of said metal catalyst; and
    (b) removing a portion of said reaction product mixture without removing said metal catalyst,
wherein said reaction product mixture comprises an organic phase and an aqueous phase, said aqueous phase comprising said metal catalyst, and wherein said portion of said product mixture being removed in step (b) is said organic phase.

2. The method of claim 1, further comprising after step (b) the step of removing at least a portion of water from said aqueous phase without removing said metal catalyst.

3. The method of claim 1, further comprising after step (b) the step of concentrating said aqueous phase into a solid wherein said solid comprises said metal catalyst.

4. A method of preparing a para-brominated hydroxyaromatic compound by an oxybromination reaction, said method comprising:
    (a) contacting in a reaction mixture a hydroxyaromatic compound with oxygen and a bromine compound selected from the group of hydrogen bromide, elemental bromine, ionic bromide salts, and mixtures thereof, in an acidic medium, in the presence of a metal catalyst selected from the group consisting of elemental copper, copper compounds, and one or more compounds or complexes of Group IV-VIII transition metals of the Periodic Table of Elements, to produce a two-phase reaction product mixture comprising an organic phase and an aqueous phase, wherein said organic phase comprises said para-brominated hydroxyaromatic compound, a corresponding ortho-brominated hydroxyaromatic compound, and unreacted said hydroxyaromatic compound, and wherein said aqueous phase comprises said metal catalyst, unreacted said bromine compound, and said acidic medium;
    (b) separating said organic phase of said product mixture from said aqueous phase, followed by optionally removing at least a portion of water from said aqueous phase; and
    (c) recycling at least a portion of said metal catalyst in said aqueous phase from which at least a portion of water has optionally been removed, to a further oxybromination reaction of additional said hydroxyaromatic compound employing oxygen and said bromine compound in said acidic medium.

5. The method of claim 4, wherein said hydroxyaromatic compound is selected from the group consisting of phenol, o-cresol, and m-cresol, wherein aqueous hydrogen bromide is said acidic medium and said bromine compound, wherein oxygen in the form of pressurized air is employed, and wherein said metal catalyst is cupric bromide ($CuBr_2$).

6. The method of claim 4, further comprising the step of removing said para-brominated hydroxyaromatic compound from said organic phase.

7. The method of claim 4, wherein step (c) further comprises the step of recycling said unreacted said bromine compound, said acidic medium, and any residual said unreacted said hydroxyaromatic compound in said aqueous phase to said further oxybromination reaction.

8. The method of claim 4, further comprising prior to step (c) the steps of:
    (i) washing said organic phase with water at least one time to remove any traces of unreacted bromine compound and any traces of said metal catalyst;
    (ii) removing said wash water from said organic phase;
    (iii) combining said wash water with said aqueous phase, and optionally removing a portion of water from said combined aqueous phase and wash water; and
    (iv) recycling said combined aqueous phase and wash water, wherein a portion of water has optionally been removed, in step (c) to said further oxybromination reaction.

9. The method of claim 4, further comprising after step (b) the steps of
    (i) removing a stream from said organic phase comprising said corresponding ortho-brominated hydroxyaromatic compound;
    (ii) contacting said stream with additional said hydroxyaromatic compound and aqueous hydrogen bromide to form a pre-equilibration mixture; and
    (iii) heating said pre-equilibration mixture at a temperature ranging from about 25° C. to about 200° C. to form a post equilibration solution comprising said corresponding ortho-brominated hydroxyaromatic compound, said para-brominated hydroxyaromatic compound, unused said hydroxyaromatic compound, and said aqueous hydrogen bromide.

10. The method of claim 9, further comprising the step of recycling said post-equilibration solution to a further oxybromination reaction of said unused hydroxyaromatic compound and additional said hydroxyaromatic compound employing said metal catalyst, oxygen, and said aqueous hydrogen bromide as said bromine source and said acidic medium.

11. The method of claim 9, wherein said stream further comprises said para-brominated hydroxyaromatic from said organic phase.

12. The method of claim 9, wherein said stream further comprises said unreacted hydroxyaromatic compound from said organic phase.

13. The method of claim 9, further comprising the step of removing said para-brominated hydroxyaromatic compound from said post equilibration solution.

14. The method of claim 9, wherein aqueous hydrogen bromide is said bromine compound and said acidic medium, and wherein said aqueous hydrogen bromide in step (ii) is provided by removing said unreacted aqueous hydrogen bromide from said aqueous phase and recycling said removed unreacted aqueous hydrogen bromide in step (ii).

15. A method of preparing a para-brominated hydroxyaromatic compound by an oxybromination reaction, said method comprising:
(a) contacting in a reaction mixture a hydroxyaromatic compound with oxygen and a bromine compound selected from the group of hydrogen bromide, elemental bromine, ionic bromide salts, and mixtures thereof, in an acidic medium and in a volatile organic solvent, in the presence of a metal catalyst selected from the group consisting of elemental copper, copper compounds, and one or more compounds or complexes of Group IV-VIII transition metals of the Periodic Table of Elements, to produce a reaction product mixture comprising said metal catalyst and a product-containing liquid comprising said para-brominated hydroxyaromatic compound, a corresponding ortho-brominated hydroxyaromatic compound, unreacted said hydroxyaromatic compound, unreacted said bromine compound, said acidic medium, and said volatile organic solvent;
(b) removing a major portion of said product-containing liquid from said reaction product mixture, wherein the removed major portion of said product-containing liquid comprises said corresponding ortho-brominated hydroxyaromatic compound, at least a portion of said para-brominated hydroxyaromatic compound, and a major portion of said unreacted hydroxyaromatic compound, and wherein the remaining said reaction product mixture comprises said metal catalyst and remaining said product-containing liquid comprising any residual para-brominated hydroxyaromatic compound, and residual said unreacted hydroxyaromatic compound; and
(c) recycling at least a portion of said metal catalyst from said remaining reaction product mixture to a further oxybromination reaction of additional said hydroxyaromatic compound employing oxygen and said bromine compound in said acidic medium.

16. The method of claim 15, wherein said hydroxyaromatic compound is selected from the group consisting of phenol, o-cresol, and m-cresol, wherein aqueous hydrogen bromide is said acidic medium and said bromine compound, wherein oxygen in the form of pressurized air is employed, and wherein said metal catalyst is cupric bromide ($CuBr_2$).

17. The method of claim 15, wherein aqueous hydrogen bromide is said acidic medium and said bromine compound, and wherein said method further comprises prior to step (b), the step of removing said unreacted said aqueous hydrogen bromide from said product-containing liquid and recycling said removed unreacted said aqueous hydrogen bromide to said further oxybromination reaction.

18. The method of claim 15, further comprising after step (b) the step of removing at least a portion of said para-brominated hydroxyaromatic compound from said removed major portion of said product-containing liquid.

19. The method of claim 15, further comprising prior to step (c) the steps of
(i) washing said removed major portion of said product-containing liquid with water at least one time to remove any said unreacted bromine compound, any said acidic medium, and any traces of said metal catalyst;
(ii) removing said wash water from said removed major portion of said product-containing liquid, and optionally removing a portion of water from said wash water; and
(iii) recycling said wash water, wherein a portion of water has optionally been removed, in step (c) to said further oxybromination reaction.

20. The method of claim 15, wherein said volatile organic solvent is selected from the group consisting of acetonitrile, chloroform, ethyl acetate, o-dichlorobenzene, acetic acid, and propionic acid.

21. The method of claim 15, further comprising prior to step (b) the step of removing said polar organic solvent from said product-containing liquid and recycling said removed polar organic solvent to said further oxybromination reaction.

22. The method of claim 15, further comprising after step (b) the steps of
(i) removing a stream from said removed major portion of said product-containing liquid, wherein said stream comprises said corresponding ortho-brominated hydroxyaromatic compound;
(ii) contacting said stream with additional said hydroxyaromatic compound and aqueous hydrogen bromide to form a pre-equilibration mixture; and
(iii) heating said pre-equilibration mixture at a temperature ranging from about 25° C. to about 200° C. to form a post equilibration solution comprising said corresponding ortho-brominated hydroxyaromatic compound and said para-brominated hydroxyaromatic compound, unused said hydroxyaromatic compound, and said aqueous hydrogen bromide.

23. The method of claim 22, further comprising recycling said post-equilibration solution to a further oxybromination reaction of said unused hydroxyaromatic compound and additional said hydroxyaromatic compound employing said metal catalyst, oxygen, and said aqueous hydrogen bromide, as said bromine compound in said acidic medium.

24. The method of claim 22, wherein said stream further comprises said para-brominated hydroxyaromatic from said removed major portion of said product-containing liquid.

25. The method of claim 22, wherein said stream further comprises said major portion of said unreacted hydroxyaromatic compound from said removed major portion of said product-containing liquid.

26. The method of claim 22, wherein said aqueous hydrogen bromide is said bromine compound in said acidic medium, and wherein said stream further comprises said unreacted said aqueous hydrogen bromide from said product-containing liquid.

27. The method of claim 22, further comprising the step of removing said para-brominated hydroxyaromatic compound from said post equilibration solution.

* * * * *